(12) United States Patent
Kawasaki et al.

(10) Patent No.: US 10,736,514 B2
(45) Date of Patent: Aug. 11, 2020

(54) STAGE DETERMINATION SUPPORT SYSTEM

(71) Applicant: Toshiba Medical Systems Corporation, Otawara-shi (JP)

(72) Inventors: Tomohiro Kawasaki, Otawara (JP); Yoshihiro Ikeda, Sakura (JP); Shigeharu Ohyu, Yaita (JP); Kensuke Shinoda, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 1605 days.

(21) Appl. No.: 14/304,183

(22) Filed: Jun. 13, 2014

(65) Prior Publication Data

US 2014/0296691 A1 Oct. 2, 2014

Related U.S. Application Data

(63) Continuation of application No. PCT/JP2013/081978, filed on Nov. 27, 2013.

(30) Foreign Application Priority Data

Nov. 27, 2012 (JP) .................................. 2012-258349

(51) Int. Cl.
*A61B 5/02* (2006.01)
*A61B 5/00* (2006.01)
(Continued)

(52) U.S. Cl.
CPC .............. *A61B 5/02* (2013.01); *A61B 5/0263* (2013.01); *A61B 5/055* (2013.01);
(Continued)

(58) Field of Classification Search
CPC combination set(s) only.
See application file for complete search history.

(56) References Cited

U.S. PATENT DOCUMENTS 6,081,612 A * 6/2000 Gutkowicz-Krusin ......................
A61B 5/0071
382/128
6,901,277 B2 * 5/2005 Kaufman ............... A61B 5/411
128/922

(Continued)

FOREIGN PATENT DOCUMENTS

JP 2012-512729 A 6/2012
WO WO 2011/058459 A1 5/2011

OTHER PUBLICATIONS

International Search Report dated Jan. 28, 2014 for PCT/JP2013/081978 Filed on Nov. 27, 2013 with English Translation.

(Continued)

*Primary Examiner* — Boniface N Nganga
(74) *Attorney, Agent, or Firm* — Oblon, McClelland, Maier & Neustadt, L.L.P.

(57) ABSTRACT

A stage determination support system according to an embodiment includes devices. The storage device stores a plurality of kinds of functional images of a subject. The first determination device determines a degree of each of a plurality of kinds of analysis indices relating to a disease, based on at least the functional images among functional images and the morphological images. The second determination device determines, based on each of determination results and a predetermined stage determination rule, a stage corresponding to the determination result with respect to each of the analysis indices. The calculation device calculates, with respect to each of the stages, a value indicative of a possibility that the disease corresponds to the stage, based on each of determination results.

11 Claims, 10 Drawing Sheets

(51) Int. Cl.
  *A61B 5/055* (2006.01)
  *A61B 5/145* (2006.01)
  *A61B 5/026* (2006.01)
  *A61B 6/03* (2006.01)
  *A61B 6/00* (2006.01)

(52) U.S. Cl.
  CPC ........ *A61B 5/14542* (2013.01); *A61B 5/4064* (2013.01); *A61B 6/032* (2013.01); *A61B 6/037* (2013.01); *A61B 6/504* (2013.01); *A61B 2576/026* (2013.01)

(56) References Cited

U.S. PATENT DOCUMENTS

| | | | |
|---|---|---|---|
| 7,756,562 B2* | 7/2010 | Kimura | A61B 5/0263 600/407 |
| 2004/0106864 A1* | 6/2004 | Rose | A61B 5/7264 600/410 |
| 2004/0127799 A1 | 7/2004 | Sorensen et al. | |
| 2004/0147840 A1* | 7/2004 | Duggirala | A61B 8/00 600/437 |
| 2005/0065432 A1* | 3/2005 | Kimura | A61B 5/0263 600/420 |
| 2008/0118122 A1* | 5/2008 | Sirohey | G06T 7/0012 382/128 |
| 2011/0129129 A1* | 6/2011 | Avinash | A61B 5/04 382/128 |
| 2011/0229003 A1* | 9/2011 | Yang | A61B 5/055 382/131 |
| 2012/0288180 A1 | 11/2012 | Bredno et al. | |

OTHER PUBLICATIONS

International Written Opinion dated Jan. 28, 2014 for PCT/JP2013/081978 Filed on Nov. 27, 2013.

Satoshi Minoshima et al., "Anatomic Standardization: Linear Scaling and Nonlinear Warping of Functional Brain Images," The Journal of Nuclear Medicine, 1994, vol. 35, pp. 1528-1537.

Karl J. Friston, et al., "Spatial registration and normalization of images", The Wellcome Dept. of Cognitive Neurology, The Institute of Neurology, 1995, pp. 1-46.

John Ashburner et al., "Nonlinear Spatial Normalization Using Basis Functions," Functional Imaging Laboratory, Wellcome Department of Cognitive Neurology, Institute of Neurology, Human Brain Mapping, 1999, pp. 7:254-266.

W J Powers et al., "Positron emission tomography and its application to the study of cerebrovascular disease in man," Stroke, American Heart Association, 1985, pp. 16:361-376.

* cited by examiner

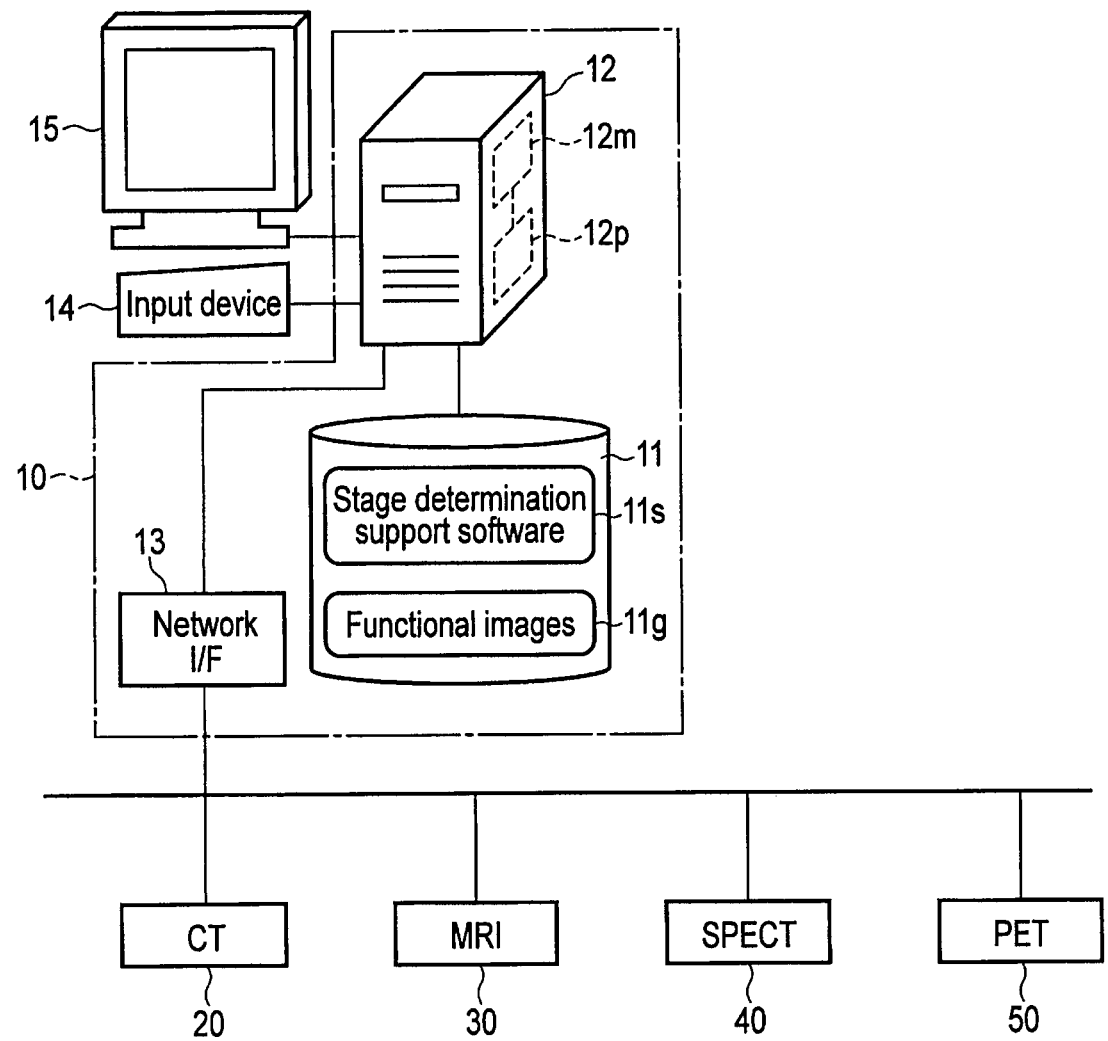
F I G. 1

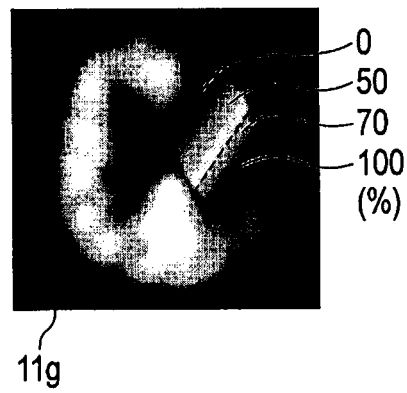
F I G. 10A
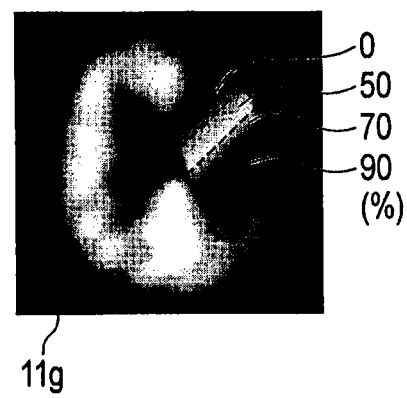
F I G. 10B

STAGE DETERMINATION SUPPORT SYSTEM

CROSS-REFERENCE TO RELATED APPLICATIONS

This is a Continuation Application of PCT application No. PCT/JP2013/081978, filed on Nov. 27, 2013, which was published under PCT Article 21(2) in Japanese.

This application is based upon and claims the benefit of priority from Japanese Patent Application No. 2012-258349, filed on Nov. 27, 2012; the entire contents of which are incorporated herein by reference.

FIELD

Embodiments described herein relate generally to a stage determination support system.

BACKGROUND

In recent years, it has become possible to determine a disease of the heart, brain, etc., by observing various functional images. For example, when cerebral ischemia diseases, such as acute-phase cerebral infarction, transient ischemic attack and chronic head-and-neck angiostenosis, are to be diagnosed, cerebral circulation metabolism amounts are evaluated based on perfusion images as two-dimensional or three-dimensional images acquired by various kinds of medical diagnostic imaging apparatuses.

As concrete analysis indices of the cerebral circulation metabolism amounts, there are such kinds of indices as a cerebral blood flow CBF [ml/100 g/min], a cerebral blood volume CBV [ml/100 g], a cerebral oxygen extraction fraction OEF [%], and a cerebral metabolic rate of oxygen CMRO2 [ml/100 g/min]. CBF is an abbreviation for Cerebral Blood Flow, and CBV for Cerebral Blood Volume. OEF is an abbreviation for Cerebral Oxygen Extraction Fraction, and CMRO2 for Cerebral Metabolic Rate of Oxygen.

In usual cases, a doctor observes magnitudes of these analysis indices in an ischemia region on a plurality of functional images, thereby comprehensively judging a severity of cerebral circulation metabolism, and deciding on courses of treatment.

Of the respective analysis indices, the magnitudes of the cerebral blood flow CBF and cerebral blood volume CBV are observed on perfusion images. Incidentally, the perfusion images are obtained from, for example, an X-ray CT (computed tomography) apparatus, an MRI (magnetic resonance imaging) apparatus, a SPECT (single photon emission CT) apparatus or a PET (positron emission tomography) apparatus.

In addition, of the respective analysis indices, the magnitudes of the cerebral oxygen extraction fraction OEF and cerebral metabolic rate of oxygen CMRO2 are observed on PET images which are obtained by, in particular, the PET apparatus.

As one index serving as a criterion for the doctor to determine the severity of the cerebral circulation metabolism after the observation of the magnitude of each analysis index, there is a typical concept of severity determination, which is called stage classification of Powers. The Powers' stage classification is comprised of indices which classify the stage of severity into three stages, by a combination of magnitudes of the above-described various analysis indices. Specifically, in these indices, as illustrated in FIG. 11, the severity of the cerebral circulation metabolism is classified into stages I, II and III, based on the magnitudes of the above-described four analysis indices (CBF, CBV, OEF, CMRO2). In general, stage III is regarded as an untreatable state because of infarction (brain cell necrosis). Stage II corresponds to a state which is called an ischemic penumbra (reversible tissue impairment), and is regarded as a state in which normalization is possible by blood flow recovery by medical treatment. The ratio of a remaining ischemic penumbra region is important in deciding on courses of treatment.

A concrete method of stage classification is described with reference to FIG. 12. In an example shown in FIG. 12, the cerebral blood flow CBF of the diseased side (the side on which cerebral ischemia occurs) decreases, the cerebral blood volume CBV increases, the cerebral oxygen extraction fraction OEF increases and the cerebral metabolic rate of oxygen CMRO2 decreases, and thus this example corresponds to stage III and is regarded as a state of brain cell necrosis.

However, in the method of stage classification as described above, determination is not possible unless thorough consideration is given to which stage the combination of the magnitudes of the four analysis indices corresponds to. Thus, there is a possibility that time is consumed for determination, or erroneous determination is made.

In addition, in an actual clinical diagnosis, such a case occurs that a combination, which corresponds to none of the stages, occurs. In such a case, there is concern over what diagnosis result should be given.

Furthermore, when all functional images have failed to be obtained, or, conversely, when a plurality of functional images have been obtained from different medical diagnostic imaging apparatuses with respect to one analysis index, a subjective judgment tends to be given concerning information which is in excess or insufficient, and it is possible that a proper diagnosis result cannot be given.

The object is to provide a stage determination support system which can display a possibility that a disease corresponds to each of stages, based on obtained functional images, and can support stage determination by a user.

BRIEF DESCRIPTION OF THE DRAWINGS

FIG. 1 is a schematic view illustrating a stage determination support system according to a first embodiment and a peripheral configuration thereof.

FIG. 10A is a schematic view illustrating an example of an image in which regions with high possibilities of stage I are displayed by color coding in the embodiment.

FIG. 10B is a schematic view illustrating an example of an image in which regions with high possibilities of stage II are displayed by color coding in the embodiment.

DETAILED DESCRIPTION

Figure 2:
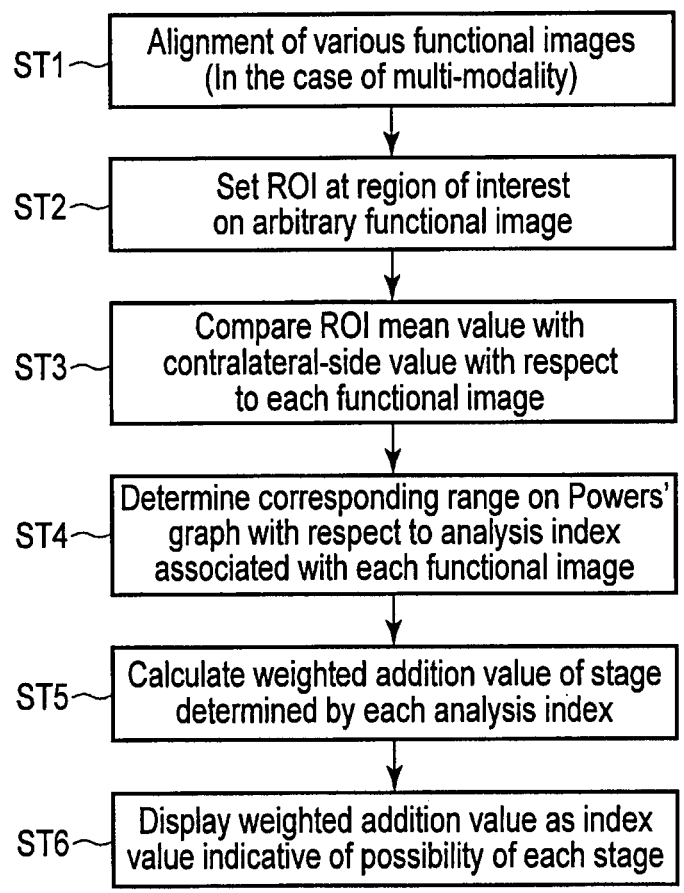
FIG. 2 is a flowchart for describing an operation in the embodiment.

In general, according to one embodiment, a stage determination support system includes a storage device, a first determination device, a second determination device and a calculation device.

The storage device stores a plurality of kinds of functional images of a subject.

The first determination device determines a degree of each of a plurality of kinds of analysis indices relating to a disease, based on at least the functional images among the functional images and morphological images.

The second determination device determines, based on each of determination results by the first determination device and a predetermined stage determination rule, a stage corresponding to the determination result with respect to each of the analysis indices.

The calculation device calculates, with respect to each of the stages, a value indicative of a possibility that the disease corresponds to the stage, based on each of determination results by the second determination device.

Stage determination support systems according to various embodiments will now be described with reference to the accompanying drawings. Each of the stage determination support systems to be described below can be implemented by a hardware configuration or by a combinational configuration of hardware resources and software. As software of the combinational configuration, a stage determination support program is used which is pre-installed in a computer over a network or from a storage medium in order to cause the computer to realize the respective functions of the stage determination support system.

First Embodiment

FIG. 1 is a schematic view illustrating a stage determination support system according to a first embodiment and a peripheral configuration thereof. The stage determination support system is a system for supporting determination as to which of a plurality stages indicative of the degree of severity a disease of a subject corresponds to. The stage determination support system is composed of, for example, a medical imaging workstation 10, an input device (e.g., a keyboard or a mouse) 14, and a monitor device 15. The medical imaging workstation 10 includes a hard disk 11, a computer 12 and a network I/F (e.g., Ethernet (trademark) card) 13. Incidentally, the term "system" in the stage determination support system may be replaced with "device", and the term "device" in the input device 14 and monitor device 15 may be replaced with "module". In addition, the stage determination support system may be realized as a client device which is connected to an image server device that collects functional images 11g via a network from devices 20 to 50, and which can read out the functional images 11g from the image server device.

The hard disk 11 stores stage determination support software (stage determination support program) 11s, and a plurality of kinds of functional images 11g and morphological images of the subject (patient). The computer 12 includes a main memory 12m and a processor 12p.

The processor 12p reads out the stage determination support software 11s and at least the functional images, among the functional images 11g and morphological images, from the hard disk 11 into the main memory (storage device) 12m, and executes the process of the stage determination support software 11s.

The processor 12p acquires the functional images 11g and morphological images from an X-ray CT apparatus 20, an MRI apparatus 30, a SPECT apparatus 40 and a PET apparatus 50 from the network I/F 13 via the network, and stores them in the hard disk 11.

The processor 12p, however, may transfer the functional images 11g and morphological images to the main memory 12m, without storing them in the hard disk 11, and may analyze the functional images 11g (and morphological images) in the main memory 12m by executing the stage determination support software 11s which has been read out from the hard disk 11.

In the meantime, the stage determination support software 11s includes a stage determination support program which is executed by the processor 12p in order to cause the computer 12 to realize a first determination function, a second determination function, a calculation function and a display function. Specifically, the stage determination support software 11s and the processor 12p constitute a first determination device, a second determination device and a calculation device. The stage determination support software 11s, the processor 12p and the monitor device 15 constitute a display device. Incidentally, there is a case in which the monitor device 15 is disposed at a place which is at a large distance from the medical imaging workstation 10. In this case, the display function may be omitted from the stage determination support program.

The first determination function is a function for determining the degree of each of a plurality of kinds of analysis indices relating to a disease, based on at least the functional images 11g among the functional images 11g and morphological images in the main memory 12m. For example, based on the functional images 11g, the first determination function determines the degree of each of the plural kinds of analysis indices relating to a disease, by comparison with each of a plurality of kinds of analysis indices relating to a region of the subject, which is regarded as normal. As the disease, for example, a cerebral ischemia disease is applicable. As the plural kinds of analysis indices, when these are based on the functional images, for example, a cerebral blood volume CBV, a cerebral blood flow CBF, a cerebral oxygen extraction fraction OEF and a cerebral metabolic rate of oxygen CMRO2 are applicable.

However, it is not necessary that all of the analysis indices be based on the functional images. For example, some of all the analysis indices may be based on morphological images.

The same applies to the respective embodiments to be described below. As the analysis indices based on morphological images, for example, Early CT Sign or CTA (CT Angiography) is usable.

Figure 13:
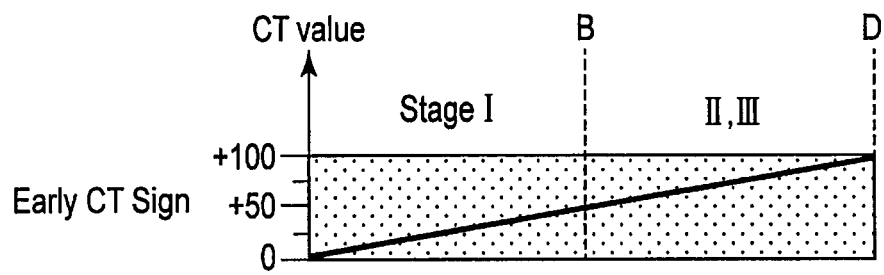
FIG. 13 is a schematic view for explaining determination of a corresponding range on stage classification by an analysis index based on a morphological image in the embodiment.

In the Early CT Sign, for example, as illustrated in FIG. 13, when a CT value is higher than a reference value B, this corresponds to stages II and III. When the CT value is not higher than the reference value B, this corresponds to stage I.

However, in the Early CT Sign, too, determination in three stages, or stages I, II and III, is possible.

In further detail, there are the following three determination criteria for the Early CT Sign:
(1) An indefinite boundary of white matter/gray matter,
(2) Loss of sulci, and
(3) A high absorption region of an occluded artery.

In this case, it is estimated that a criterion, by which determination is possible with a simple CT threshold, is only (3).

When the criterion of (3) is used, if there are two choices of "high absorption region or not", the case of high absorption corresponds to all of stages I, II and III.

In this case, in the example of FIG. 13, even in the case of two choices of "stage I" or "stages II and III", distinction is made based on the degree of height of the CT value. However, determination may also be made by three stages of stages I, II and III.

For example, in the case of using the Early CT Sign, like determination of other functional images, determination may be made by plotting a large/small comparison result (large, small, substantially equal) with a contralateral side on the ordinate. Thereby, even in the case where determination by the absolute value of the CT value is hard to be done, it is possible to determine the stage by three stages of I, II and III.

Figure 14:
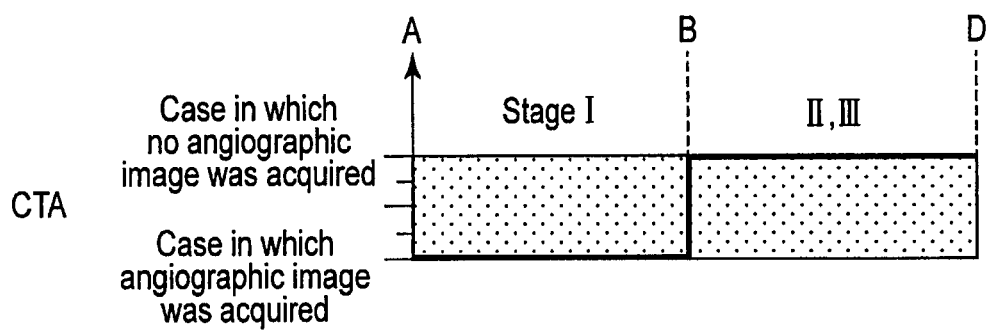
FIG. 14 is a schematic view for explaining determination of a corresponding range on stage classification by an analysis index based on a morphological image in the embodiment.
Figure 15:
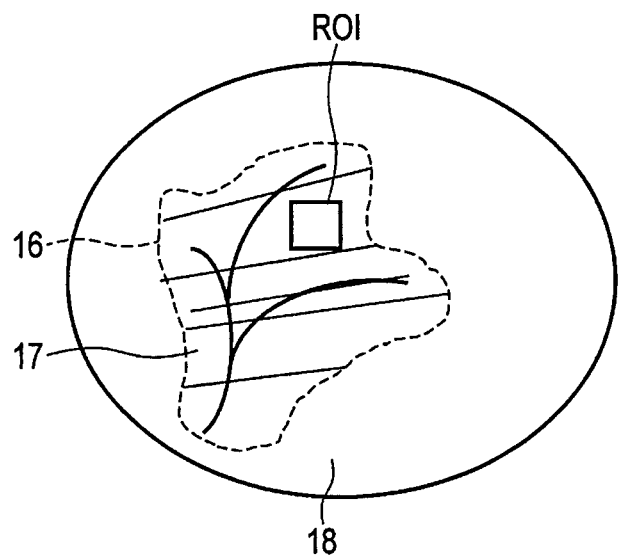
FIG. 15 is a schematic view illustrating an example of a morphological image using CTA.

In the CTA, for example, as illustrated in FIG. 14 and FIG. 15, a case 17, in which an angiographic image of blood vessels in a dominant region 16 was acquired, corresponds to stage I. A case 18, in which no angiographic image of blood vessels in the dominant region 16 was acquired, corresponds to stages II and III. Whether an angiographic image of blood vessels in the dominant region 16 is acquired or not is determined, for example, with respect to each region of interest ROI. In the case where no angiographic image was obtained, since the blood vessel itself in the dominant region 16 is not visible, no identification can be made. Thus, in this case, too, a comparison with a contralateral side needs to be made. In the case where a distance between a disease-side ROI and a nearest blood vessel is larger than a distance between a contralateral-side ROI and a nearest blood vessel, it is determined that a blood vessel, which is normally dominant, is not angiographed, so that determination of a higher stage may be made. In this case, too, determination may be made by three stages I, II and III, based on the magnitude of the difference in distance, by plotting on the ordinate a large/small comparison result (large, small, substantially equal) with the contralateral side of the shortest distance from the ROI to the angiographed blood vessel. Incidentally, when the distance from the ROI to the angiographed blood vessel is smaller than, or substantially equal to, the distance on the contralateral side, this corresponds to none of stages I, II and III.

In addition, the first determination function may be a function of executing determination of the degree, for example, by setting the following (a), (b), (c) and (d) as determination target regions. Incidentally, in the present embodiment, the case of setting (a) as a determination target region is described by way of example.
(a) A region of interest ROI which was set in each functional image 11g by the user.
(b) A region which was determined to be abnormal by comparison of pixel values with a normal region represented by each functional image 11g.
(c) Regions obtained by dividing the entire tissue represented by each functional image 11g into a plurality of segments.
(d) Each pixel unit on each functional image 11g.

Furthermore, the first determination function may be a function of executing determination of the degree by comparing pixel values between the determination target region (the above (a), (b), (c) or (d)) in each functional image 11g and a region regarded as normal. In this case, the region regarded as normal may be, for example, a contralateral-side region which is in a left-and-right symmetric relationship with the determination target region, or a partial region of the cerebellum (which is not prone to infarction, with a low possibility of suffering ischemia).

Further, in the case where the stage determination support program further causes the computer 12 to realize an alignment function for executing alignment of each functional image 11g, the first determination function may be a function of executing determination of the degree, based on each functional image 11g for which the alignment was executed.

The second determination function is a function of determining the stage corresponding to the determination result with respect to each analysis index, based on each determination result by the first determination function and a predetermined stage determination rule. As the stage determination rule, for example, it is possible to apply a determination rule for executing the Powers' stage classification on a cerebral ischemia disease, based on the cerebral blood volume CBV, cerebral blood flow CBF, cerebral oxygen extraction fraction OEF and cerebral metabolic rate of oxygen CMRO2.

The calculation function is a function of calculating, with respect to each of the stages, a value indicative of a possibility that a disease corresponds to the stage, based on each determination result by the second determination function. This calculation function may be a function of calculating a value indicative of the possibility, for example, by executing weighted addition of the respective determination results by the second determination function.

The display function is a function of displaying the calculated value on the monitor device 15 with respect to each of the stages. The display function may be a function of executing, by the monitor device 15, numerical display, graph display or color scale display, based on the calculated value.

Next, the operation of the stage determination support system with the above-described structure will be described with reference to a flowchart of FIG. 2. Incidentally, it is assumed that, in the medical imaging workstation 10 of the stage determination support system, by the operation of the input device 14 by the user, the processor 12p has read out the stage determination support software 11s from the hard disk 11 into the main memory 12m, and is executing the stage determination support software 11s. In addition, in the present embodiment, the case of using at least the functional images 11g, among the functional images 11g and morphological images, is described by way of example.

In step ST1, in the medical imaging workstation 10, by the operation of the input device 14 by the user, the processor 12p reads out the functional images 11g, which are associated with the respective analysis indices of the cerebral circulation metabolism amounts designated by the user, from the hard disk 11 into the main memory 12m. Further, the processor 12p sends out the functional images 11g to the monitor device 15, and the monitor 15 displays the functional images 11g.

Subsequently, the processor 12p executes alignment of the functional images 11g, based on the anatomical form. As the method of alignment, use may be made of a 3D-SSP (stereotactic surface projection) method or an SPM (statistical parametric mapping) method, which is a publicly known, typical method of alignment with a standard brain.

The 3D-SSP method is described, for example, in document [1].

[1] S Minoshima, R A Koeppe, K A Frey, et al., "Anatomic standardization: Linear scaling and nonlinear warping of functional brain images", J Nucl Med, 35(9), 1528-1537, (1994).

The SPM method is described, for example, in documents [2] and [3].

[2] K J Friston, J Ashburner, C D Frith, et al., "Spatial registration and normalization of images", Human Brain Mapping, 2, 165-189, (1995).

[3] J Ashburner, and K J Friston, "Nonlinear spatial normalization using basis functions", Hum Brain Mapp, 7(4), 254-266, (1999).

Figure 11:
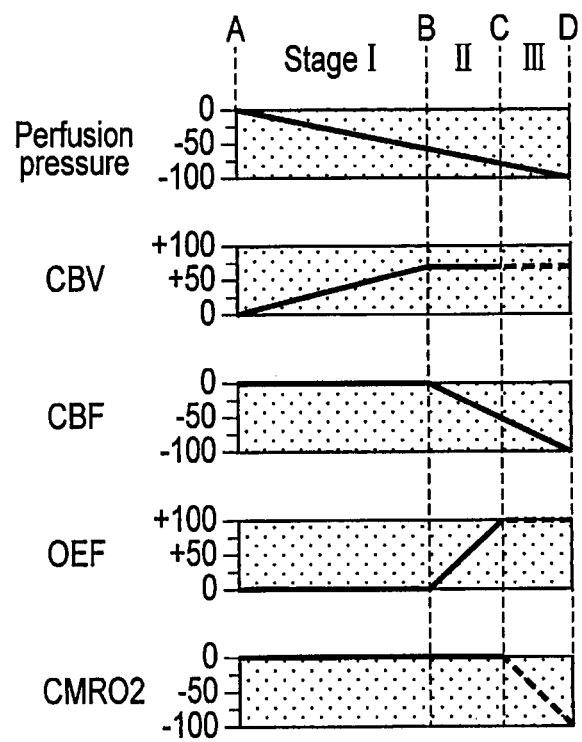
FIG. 11 is a schematic view illustrating general Powers' stage classification.
Figure 12:
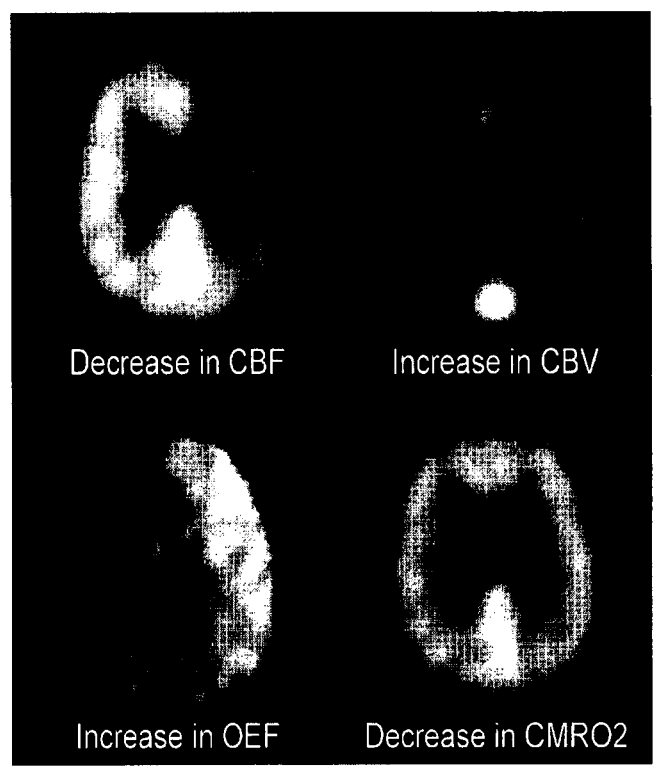
FIG. 12 is a view illustrating examples of cerebral circulation metabolism amounts in general internal carotid artery stenosis.

The number of functional images 11g, which are associated with one analysis index, may be one, plural, or zero. Specifically, perfusion images, which are obtained from the X-ray CT apparatus 20, MRI apparatus 30, SPECT apparatus 40 or PET apparatus 50, are mainly used as the functional images 11g which are associated with the cerebral blood flow CBF and cerebral blood volume CBV. In addition, PET images are used as the functional images 11g which are associated with the cerebral oxygen extraction fraction OEF and cerebral metabolic rate of oxygen CMRO2. Further, as is understood from FIG. 11, since the decrease in cerebral metabolic rate of oxygen CMRO2 can be regarded as a state which is equivalent to brain cell necrosis, a high signal value of a diffusion weighted image DWI of MRI may be substituted as an analysis index, in place of the functional image 11g.

In the meantime, no misalignment occurs between a plurality of functional images 11g which are obtained by analysis with use of data obtained by one-time imaging by the same medical diagnostic imaging apparatus, 20 to 50. Thus, the present alignment process is not needed in this case.

In step ST2, the processor 12p displays all functional images 11g, which have been designated by the user, on the screen of the monitor device 15. By the operation of the input device 14 by the user, the processor 12p sets a region of interest ROI at a region on an arbitrary displayed functional image 11g, which is considered to be an ischemia state with a low signal or a high signal, compared to the contralateral side.

Figure 3:
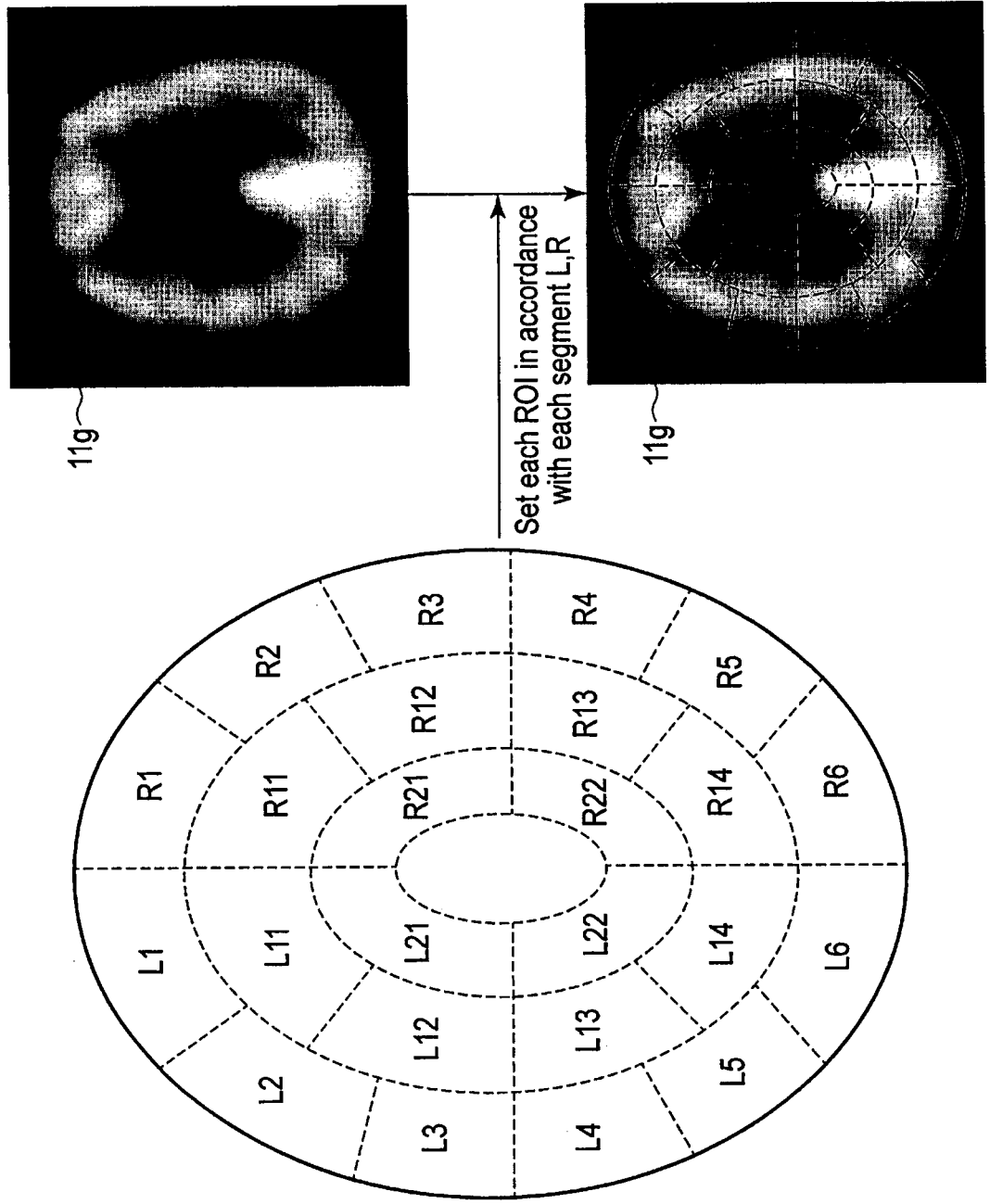
FIG. 3 is a schematic view illustrating an example of segments into which the brain is divided in the embodiment.

Incidentally, the shape of the region of interest ROI may be elliptic, etc., or may be arbitrary. In addition, the processor 12p may detect a region, at which a left-and-right difference of signal values is large, by an internal process, and may automatically set the region of interest ROI at this region. Alternatively, as illustrated in FIG. 3 by way of example, the whole brain (or only the outer peripheral region of the brain) may be divided in advance into a plurality of fine segments L1, L2, . . . , R1, R2, . . . , and a plurality of regions of interest ROI may be set in a plurality of regions which individually correspond to the plural segments L1, L2, . . . , R1, R2, . . . , on the functional image 11g. In the meantime, from the standpoint of setting the regions of interest ROI in left-and-right symmetry, it is preferable to divide the segments L1, L2, . . . , R1, R2, . . . , in left-and-right symmetry.

Figure 4:
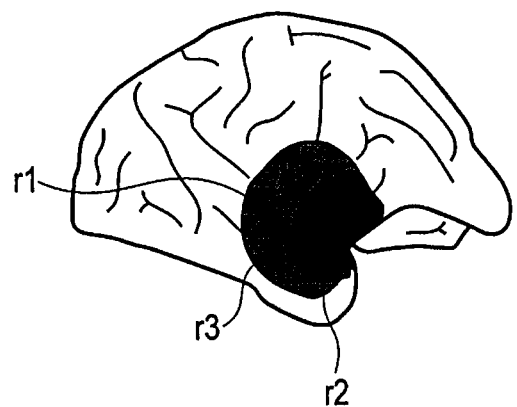
FIG. 4 is a schematic view for explaining a general ischemic penumbra and a central-part infarction region.

In addition, it is also possible to set a plurality of regions of interest ROI, in accordance with the operation of the input device 14 by the user. In the case where a plurality of regions of interest ROI, which are set by the user, overlap, the larger region of interest ROI is set to be a region from which the smaller region of interest ROI is excluded. This is based on the assumption of the case in which, as shown in FIG. 4, stage determination is to be individually executed for regions r2 and r3, namely, a central-part infarction (brain cell necrosis) region (ischemic core) r2 in a cerebral ischemia region r1, and the other ischemic penumbra region (ischemic penumbra) r3.

In step ST3, the processor 12p sets a region of interest ROI, which corresponds to the region of interest ROI that is set on the diseased side (ischemia side of brain), on an unaffected side (normal side of brain) in left-and-right symmetry, and compares mean values of the left and right regions of interest ROI with respect to each functional image 11g. The processor 12p determines the degree as to whether the mean value of the region of interest ROI on the diseased side is "large", "small" or "substantially equal", compared to the unaffected side. As regards thresholds for determining "large", "small" and "substantially equal", it is determined that the degree is "large" if the ratio to the unaffected side is 120% or more, the degree is "small" if the ratio is less than 70%, and the degree is "substantially equal" if the ratio is 70% or more, and less than 120%. Further, a case in which both sides suffer ischemia can be envisaged. In order to make the determination feasible even when both sides suffer ischemia, it is possible to set a region of interest ROI of a normal region in, e.g., the cerebellum with a low possibility of suffering ischemia, and to compare this region of interest ROI with the ischemia region, instead of the determination based on the left-and-right ratio.

Figure 5:
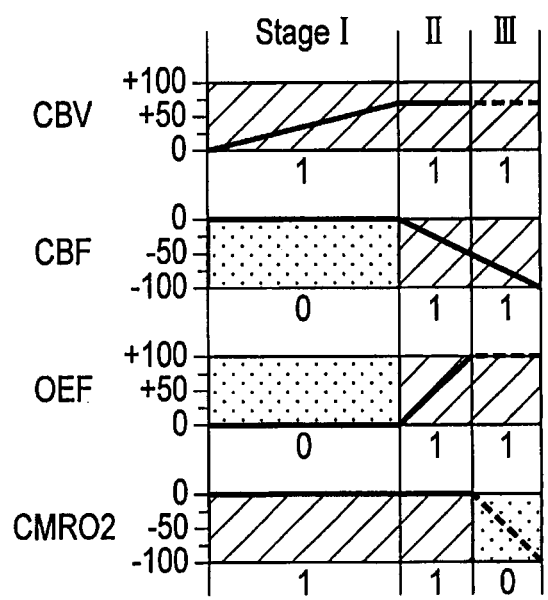
FIG. 5 is a schematic view for explaining determination of a corresponding range on stage classification in the embodiment.

In step ST4, with respect to each functional image 11g, based on the determination result (large, small, substantially equal) by the comparison with the unaffected side and the stage determination rule on the Powers' stage classification, the processor 12p determines the stage corresponding to this determination result with respect to each of the analysis indices. For example, in the case illustrated in FIG. 5, since the cerebral blood volume CBV has been determined to be large, it is determined that the determination result corresponds to all of the stages I, II and III, and the corresponding range is determined to be stages I to III. Since the cerebral blood flow CBF has been determined to be small, it is determined that the determination result corresponds to stages II and III, and the corresponding range is determined to be stages II and III. Since the cerebral oxygen extraction fraction OEF has been determined to be large, it is determined that the determination result corresponds to stages II and III, and the corresponding range is determined to be stages II and III. Since the cerebral metabolic rate of oxygen CMRO2 has been determined to be substantially equal, it is determined that the determination result corresponds to stages I and II, and the corresponding range is determined to be stages I and II.

In step ST5, by the operation of the input device 14 by the user, the processor 12p sets weighting factors of the respective analysis indices in advance. The weighting factors of the respective analysis indices are set at ratios corresponding to the degree of importance as decided by the user. The sum of weighting factors of the respective analysis indices is set to be 1 in this example, but the sum is not limited to this and may be, for example, 100 (the case of adding with weighting on percentage in advance).

The processor 12$p$ sets 1 or 0 in accordance with a determination result as to whether each analysis index is "corresponding" or "not corresponding", with respect to each of the stages, and the processor 12$p$ calculates weighted addition values, which are obtained by multiplying each set value (1 or 0) by a weighting factor (0.3, 0.3, 0.1, or 0.3) and adding the multiplied values, as values indicative of the possibility of each stage. For example, in the case shown in FIG. 6, the weighted addition value of stage I is calculated by 0.3×1+0.3×0+0.1×0+0.3×1=0.6. If this value is multiplied by 100 and is expressed as a percentage, the value indicative of possibility becomes 60%. The same calculation is performed for stages II and III, and 100% and 70% are obtained, respectively. Incidentally, if such weighted addition is not performed, it should suffice if all weighting factors are set at 1.

In this case, as regards the analysis index with no target functional image 11$g$, the possibility of each of stages I to III may be set to be 0, or may be calculated to be ⅓ by assuming that the possibilities of all stages I to III are equal. In addition, when a plurality of functional images 11$g$ obtained from different medical diagnostic imaging apparatuses are present in association with one analysis index, it should suffice if a plurality of results are simply added. In this manner, by adding the results of plural functional images 11$g$, such an advantageous effect can be obtained that the reliability of the likelihood of the stage possibility of the analysis index is increased.

Figure 6:
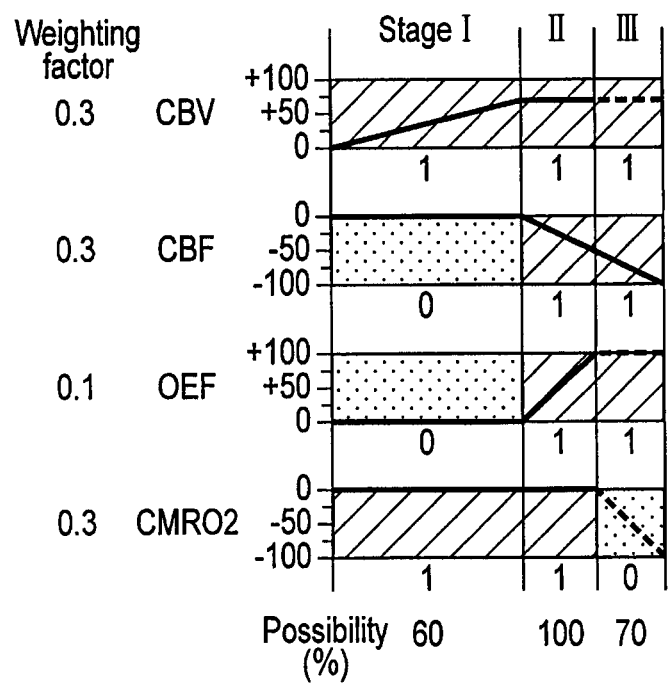
FIG. 6 is a schematic view for explaining a calculation method of a stage possibility in the embodiment.

In step ST6, the processor 12$p$ displays the calculated values on the monitor device 15 with respect to each of the stages. As regards the display method, numeral values may be displayed together with the Powers' stage classification, as shown in FIG. 6, or the calculated values may be displayed by other methods of expression, such as a bar graph, a circle graph or a color scale image.

As has been described above, according to the present embodiment, the degree of each of the analysis indices is determined based on each functional image 11$g$. Based on each determination result and a predetermined determination rule, the stage corresponding to the determination result is determined with respect to each analysis index. Based on each of the determination results, the value indicative of the corresponding possibility is calculated and displayed. By this configuration, the possibility that the disease corresponds to each stage can be displayed from the obtained functional image 11$g$, and the stage determination by the user can be supported.

In addition, by the above, since the possibility related to each stage is understandable at a glance, it is not necessary for the user to perform judgment by viewing images, and it is possible to immediately determine the stage classification objectively, without erroneous determination. Further, even in the case where a combination of analysis indices corresponds to none of the stages, the user can objectively view the height of the possibility of each stage and can determine the stage classification. Furthermore, in the case where functional images 11$g$ of plural modalities are acquired, the reliability of the value indicative of the possibility increases, and therefore the precision of determination can further be increased.

Figure 7:
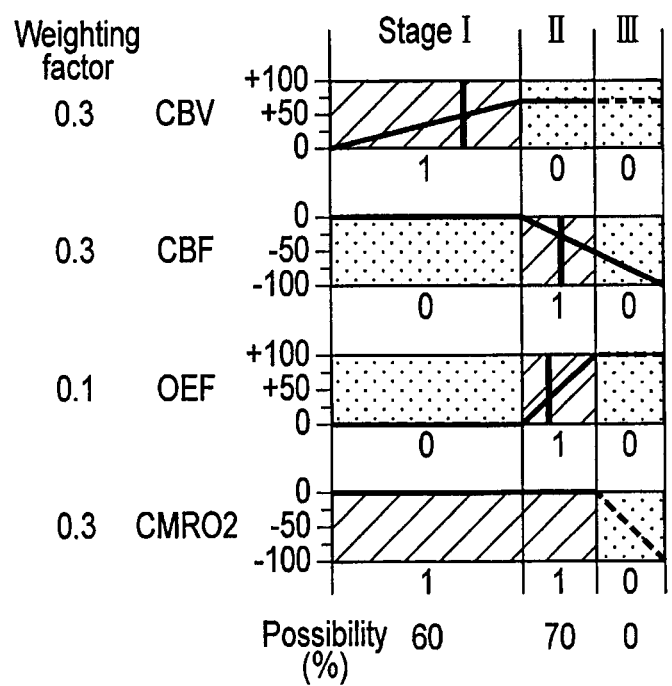
FIG. 7 is a schematic view for explaining another calculation method of the stage possibility in the embodiment.

In the meantime, the present embodiment may be modified as shown in FIG. 7. In the case of an example illustrated in FIG. 7, the degree of "large", "small" or "substantially equal" is not determined based on the ratio to the unaffected side in step ST4, but the ratio itself to the unaffected side is directly used for stage determination. For example, a maximum value (e.g., +100%) and a minimum value (e.g., −100%) of the ratio are preset by the user. The processor 12$p$ determines the stage with respect to each analysis index, based on a value indicative of the ratio to the unaffected side, with the maximum value or minimum value of the ratio being a limit value, and the range of values indicative of the ratio corresponding to the stage of each analysis index.

In the example illustrated in FIG. 7, as regards the cerebral blood volume CBV, the range of values indicative of the ratio corresponding to stage I is 0% to +74%, and the range of values indicative of the ratio corresponding to stages II and III is +75%.

As regards the cerebral blood flow CBF, the range of values indicative of the ratio corresponding to stage I is 0%, the range of values indicative of the ratio corresponding to stage II is −1% to −50%, and the range of values indicative of the ratio corresponding to stage III is −51% to −100%.

As regards the cerebral oxygen extraction fraction OEF, the range of values indicative of the ratio corresponding to stage I is 0%, the range of values indicative of the ratio corresponding to stage II is +1% to +99%, and the range of values indicative of the ratio corresponding to stage III is +100%.

As regards the cerebral metabolic rate of oxygen CMRO2, the range of values indicative of the ratio corresponding to stages I and II is 0%, and the range of values indicative of the ratio corresponding to stage III is −1% to −100%.

Accordingly, in the case of the example shown in FIG. 7, as regards the cerebral blood volume CBV, since the value indicative of the ratio to the unaffected side is +70%, stage I corresponding to the range of 0% to +74% is determined. By the same method, as regards the cerebral blood flow CBF, cerebral oxygen extraction fraction OEF and cerebral metabolic rate of oxygen CMRO2, stage II, stage II, and stages I and II are determined, respectively. The calculation method and display method of the values indicative of the possibilities of the respective stages are the same as in the method described in steps ST5 to ST6.

Second Embodiment

Next, a stage determination support system according to a second embodiment is described with reference to FIG. 1. A detailed description of the same parts as those described above is omitted, and different parts will mainly be described.

The second embodiment is a modification of the first embodiment. In this embodiment, unlike the first embodiment in which the region of interest ROI is used, the above-described first determination function, second determination function, calculation function and display function are executed by setting respective pixel units on each functional image 11$g$ as targets.

Specifically, the first determination function executes the determination of the degree, by setting respective pixel units on each functional image 11$g$ as targets in the above-described first determination function.

The second determination function executes the determination of the stage, by setting respective pixel units as targets in the above-described second determination function.

The calculation function calculates values with respect to each of the stages, by setting respective pixel units as targets.

The display function is a function of executing color-coding display so as to indicate a stage corresponding to a highest value of the values calculated with respect to each of the stages, by setting respective pixel units as targets in the above-described display function.

Other parts are the same as in the first embodiment.

Figure 8:
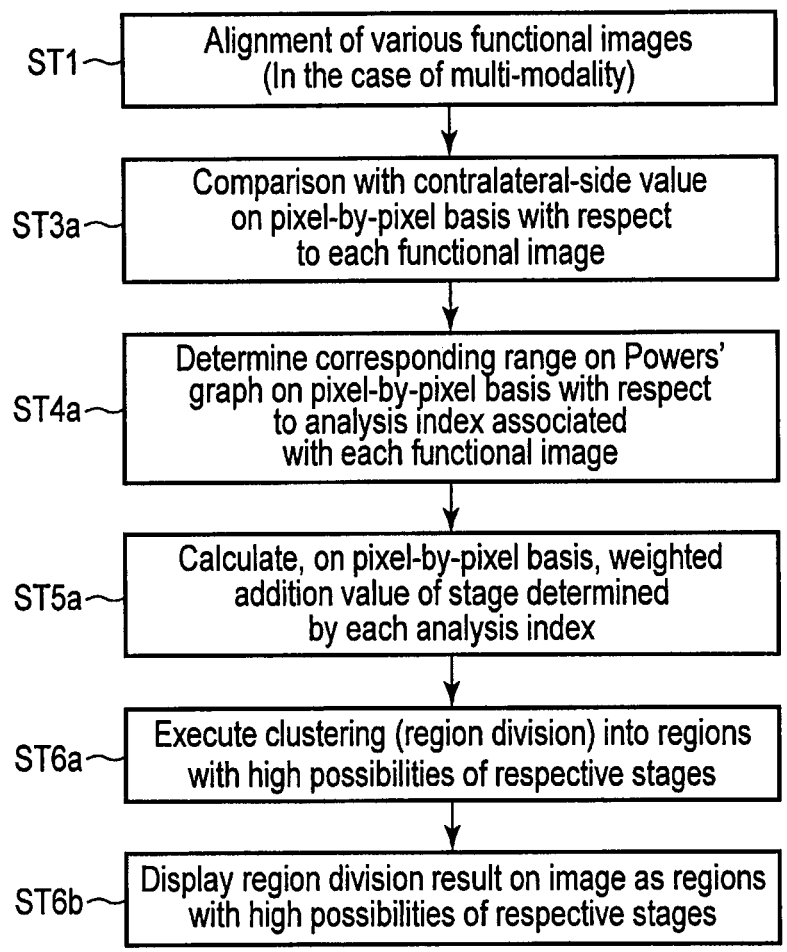
FIG. 8 is a flowchart for describing an operation in a second embodiment.

Next, referring to a flowchart of FIG. 8, a description is given of the operation of the stage determination support system configured as described above.

To begin with, the operations from the start to the alignment of each functional image 11g of step ST1 is executed similarly to the first embodiment. In addition, after the completion of step ST1, the above-described step ST2 (the setting of the region of interest ROI) is not executed.

In step ST3a, the processor 12p executes the process corresponding to the above-described step ST3 (the determination of the degree by comparison with the unaffected side with respect to each functional image 11g) on a pixel-by-pixel basis with respect to all pixels which are in left-and-right symmetry.

In step ST4a, the processor 12p executes the process corresponding to the above-described step ST4 (the determination of the stage, based on the determination result of the degree) on a pixel-by-pixel basis with respect to all pixels which are in left-and-right symmetry.

In step ST5a, the processor 12p executes the process corresponding to the above-described step ST5 (the calculation of weighted addition values indicative of the possibility of each stage, based on the determination result of the stage) on a pixel-by-pixel basis with respect to all pixels which are in left-and-right symmetry.

In step ST6a, the processor 12p determines which stage possibility is indicated by a highest value on a pixel-by-pixel basis, and executes region division (clustering) to divide the pixels with the same values of the determination results into three set regions.

Figure 9:
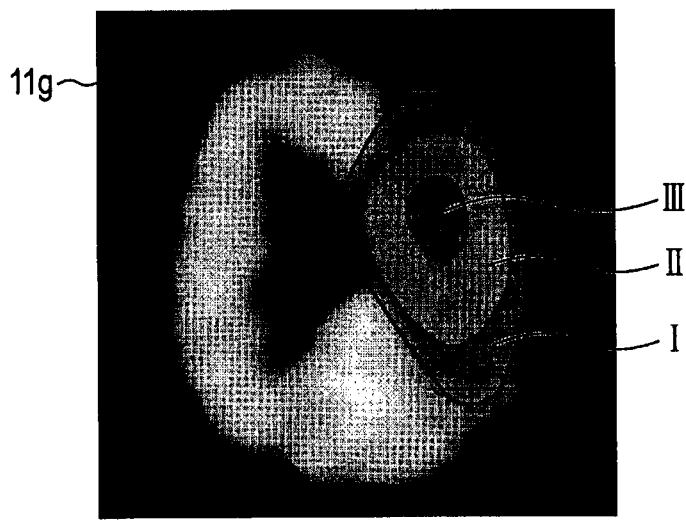
FIG. 9 is a schematic view illustrating an example of a display image of a region where the possibilities of respective stages are high in the embodiment.

In step ST6b, the processor 12p displays, by the monitor device 15, the region division result, which indicates the stages with the highest possibilities, in a color-coded manner. For example, as illustrated in FIG. 9, it is assumed that the processor 12p has obtained in step ST6a a region division result having such a shape that a central red region (stage III) is successively surrounded by an ocher region (step II) and a blue region (stage I). In step ST6b, the processor 12p creates an image in which this region division result is laid over the functional image 11g as regions with the high possibilities of the respective stages, and displays this image by the monitor device 15.

Figure 10C:
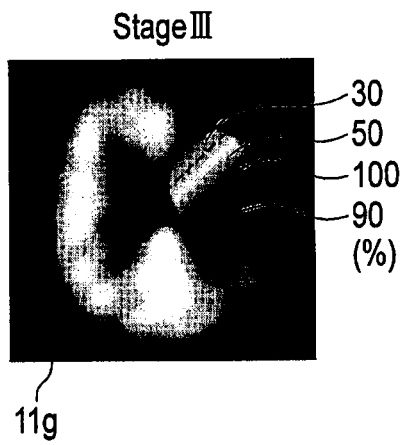
FIG. 10C is a schematic view illustrating an example of an image in which regions with high possibilities of stage III are displayed by color coding in the embodiment.

As a modification of the display method of step ST6b, there is a method of displaying such an image that the values, which indicate, with respect to each of the stages, the possibilities of all pixels that are in left-and-right symmetry, are displayed by color coding on an arbitrary functional image 11g by a method of color scaling or the like. In the examples shown in FIG. 10A, FIG. 10B and FIG. 10C, an image, in which the pixels are displayed by color coding in blue (0%), yellow (50%), brown (70%) and red (100%), is displayed over a functional image 11g of stage I. Similarly, an image, in which the pixels are displayed by color coding in blue (0%), yellow (50%), brown (70%) and purple (90%), is displayed over a functional image 11g of stage II. In addition, an image, in which the pixels are displayed by color coding in green (30%), yellow (50%), red (100%) and purple (90%), is displayed over a functional image 11g of stage III. Incidentally, for the purpose of convenience in the black and white two-color drawing, broken lines are used to represent boundaries between colors in the color-coded images. In actuality, however, there are no broken lines, and colors vary with obscure boundaries like a rainbow. In addition, the color scale images of the three stages may be displayed at the same time, as illustrated in FIG. 10A, FIG. 10B and FIG. 10C, or the color scale image of each stage may be changed and displayed.

As has been described above, according to the present embodiment, the stage determination is executed by setting each pixel unit on each functional image 11g as a target, in place of the region of interest ROI. By this configuration, in addition to the advantageous effect of the first embodiment, it is possible to display the values indicative of the possibilities of each stage on a pixel-by-pixel basis, with a higher fineness than the above-described region of interest ROI.

According to at least one of the above-described embodiments, the degree of each of analysis indices is determined based on at least the functional images 11g among the functional images 11g and morphological images. Based on each determination result and a predetermined determination rule, the stage corresponding to the determination result is determined with respect to each analysis index. Based on each of the determination results, the values indicative of the corresponding possibilities are calculated and displayed with respect to each of the stages. By this configuration, the possibility that the disease corresponds to each stage can be displayed, and the stage determination by the user can be supported.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A stage determination support system comprising:
a processor configured to
store a plurality of kinds of functional images of a subject in a memory,
determine a degree of each of a plurality of kinds of analysis indices relating to a disease, based on at least the functional images among the functional images and morphological images of a subject,
determine, based on each determined degree and a predetermined stage determination rule, a stage corresponding to the determination result with respect to each of the analysis indices, the stage being an index of rising severity of the disease, classified into three stages,
set weighting factors of each of the analysis indices, and
calculate, with respect to each of the stages, a weighted addition value, which is obtained by multiplying a determination result of each of the analysis indices by weighting factors and adding the multiplied values, the weighted addition value being a possibility, in percent value, that the disease corresponds to one of the three stages.

2. The stage determination support system according to claim 1, wherein the disease is a cerebral ischemia disease.

3. The stage determination support system according to claim 2, wherein the plurality of kinds of analysis indices are a cerebral blood volume, a cerebral blood flow, a cerebral oxygen extraction fraction, and a cerebral metabolic rate of oxygen, and the stage determination rule is a determination rule for executing stage classification of powers relating to the cerebral ischemia disease, based on the cerebral blood volume, the cerebral blood flow, the cerebral oxygen extraction fraction, and the cerebral metabolic rate of oxygen.

4. The stage determination support system according to claim 1, wherein the processor is further configured to determine the degree by setting, as determination target regions, a region of interest which is set in each of the functional images by a user, a region which is determined to be abnormal by comparison of pixel values with a normal region represented by each of the functional images, regions obtained by dividing an entire tissue represented by each of the functional images into a plurality of segments, and each of pixel units on each of the functional images.

5. The stage determination support system according to claim 1, wherein the processor is further configured to determine the degree by comparing pixel values between the determination target region and a region regarded as normal in each of the functional images.

6. The stage determination support system according to claim 5, wherein the region regarded as normal is a contralateral-side region which is in a left-and-right symmetric relationship with the determination target region in each of the functional images.

7. The stage determination support system according to claim 5, wherein the region regarded as normal is a partial region of a cerebellum.

8. The stage determination support system according to claim 1, wherein the processor is further configured to execute an alignment of each of the functional images, and determine the degree, based on each of the functional images, for which the alignment has been executed.

9. The stage determination support system according to claim 1, further comprising display device which displays the calculated value with respect to each of the stages, wherein the display device executes numerical display, graph display or color scale display, based on the calculated value.

10. The stage determination support system according to claim 1, wherein the processor is further configured to
determine the degree by setting respective pixel units on each of the functional images as targets,
determine the stage by setting the respective pixel units as targets,
calculate the value with respect to each of the stages by setting the respective pixel units as targets, and
a display device executes color-coding display indicating a stage corresponding to a highest value of the values calculated with respect to each of the stages, by setting the respective pixel units as targets.

11. A stage determination support system comprising:
a processor configured to
store a plurality of kinds of functional images of a subject in a memory,
determine a degree of each of a plurality of kinds of analysis indices relating to a disease, based on at least the functional images among the functional images and morphological images of a subject, and further, by setting respective pixel units on each of the functional images as targets,
determine, based on each determined degree and a predetermined stage determination rule, a stage corresponding to the determination result with respect to each of the analysis indices, the stage being an index of rising severity of the disease, classified into three stages,
set weighting factors of each of the analysis indices,
set the respective pixel units,
calculate, with respect to each of the stages, a weighted addition value, which is obtained by multiplying a determination result of each of the analysis indices by weighting factors and adding the multiplied values, the weighted addition value being a possibility, in percent value, that a disease progression corresponds to one of the three stages,
cluster the respective pixel units into regions of interest with high possibilities of different stages; and
a display device configured to execute color-coding display indicating a stage corresponding to each respective pixel units as targets.

* * * * *